Figure 1:
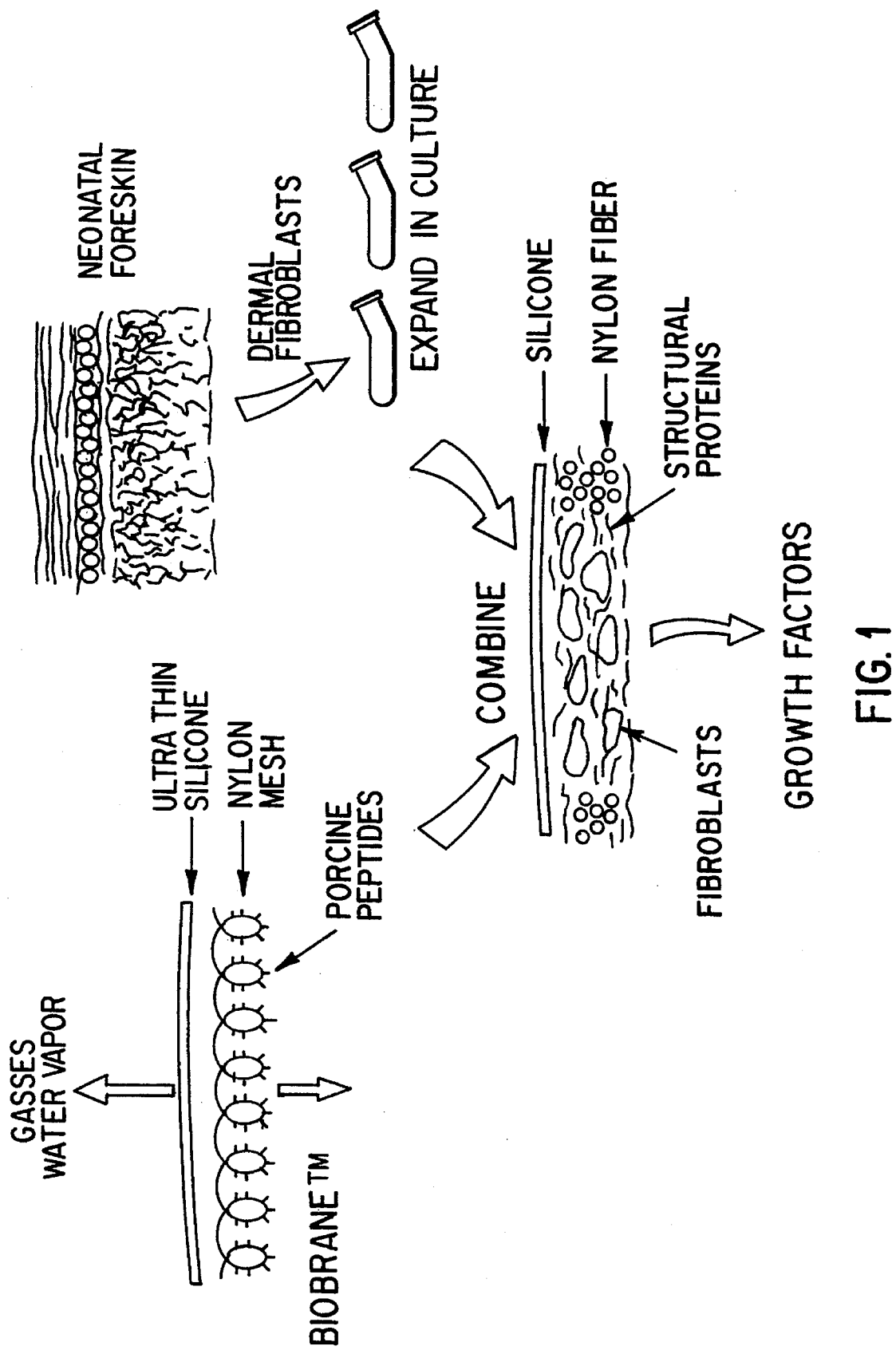

ID=1 />

United States Patent [19]
Hansbrough et al.

[11] Patent Number: 5,460,939
[45] Date of Patent: Oct. 24, 1995

[54] TEMPORARY LIVING SKIN REPLACEMENT

[75] Inventors: John F. Hansbrough, Rancho Santa Fe; Gail K. Naughton, El Cajon, both of Calif.

[73] Assignee: Advanced Tissue Sciences, Inc., La Jolla, Calif.

[21] Appl. No.: 200,140

[22] Filed: Feb. 18, 1994

Related U.S. Application Data

[60] Continuation-in-part of Ser. No. 131,361, Oct. 4, 1993, which is a division of Ser. No. 575,518, Aug. 30, 1990, Pat. No. 5,266,480, which is a division of Ser. No. 402,104, Sep. 1, 1989, Pat. No. 5,032,508, which is a continuation-in-part of Ser. No. 242,096, Sep. 8, 1988, Pat. No. 4,963,489, which is a continuation-in-part of Ser. No. 38,110, Apr. 14, 1987, abandoned, which is a continuation-in-part of Ser. No. 36,154, Apr. 3, 1987, Pat. No. 4,721,096, which is a continuation of Ser. No. 853,569, Apr. 18, 1986, abandoned.

[51] Int. Cl.$^6$ .............................. C12N 11/00; A61F 2/10; C12M 3/00
[52] U.S. Cl. .................. 435/1.1; 435/240.1; 435/240.23; 424/572; 424/574; 424/93.1; 424/93.21; 424/93.7
[58] Field of Search .................. 435/1, 2, 240.1, 435/240.2, 240.23, 240.21; 424/93 R, 95, 529, 530, 534, 572, 574, 93 B, 93 U

OTHER PUBLICATIONS

Hansbraugh, et al. 1993 Proc of the ABA 29th Annual Mtg. Mar. 24–27 Cincinnati, Ohio vol. 25.
Woodroof, "Biobrane A Biosynthetic Skin Prosthesis," from Burn Wound Coverings, published by CRC Press, Inc. ed. D. L. Wise Ph.D., in press, pp. 1–20 (No Pub. Date).
Hansbrough et al., 1993, "Evaluation of living biosynthetic temporary skin replacement: Human fibroblasts cultured on biobrane," Proceedings of the ABA Twenty–Fifth Annual Meeting Mar. 24–27, Cincinnati, Ohio, vol. 25.
Purdue et al., 1987, "Biosynthetic skin substitute versus frozen human cadaver allograft for temporary coverage of excised burn wounds," J. Trauma 27:155–157.
McHugh et al., 1986, "Therapeutic efficacy of biobrane in partial and full–thickness thermal injury," Surgery 100:661–664.
Frank and Bonaldi, 1985, "Inhibition of wound contraction: Comparison of full–thickness skin grafts, biobrane, and aspartate membranes," Annals of Plastic Surgery 14:103–110.
Zapata–Sirvent et al., 1985, "Comparison of biobrane and scarlet red dressings for treatment of donor site wounds," Archives of Surgery 120:743–745.
Hansbrough et al., 1984, "Clinical experience with biobrane biosynthetic dressing in the treatment of partial thickness burns," Burns 10:415–419.
Frank et al., 1983, "Comparison of biobrane, porcine, and human allograft as biologic dressings for burn wounds," J. Burn Care Rehab., 4:186–190.
Lin et al., 1982, "A comparison of IP–758 and biobrane in rats as temporary protective dressings on widely expanded meshed autografts," J. Burn Care Rehab. 3:220–222.
Zachary et al., 1982, "The use of topical antimicrobials combined with biobrane in burn wound infections," J. Trauma 22:833–836.
Bartlett, 1981, "Skin substitutes," J. Trauma 21:731–732.
Tavis et al., 1976, "Graft adherence to de–epithelialized surfaces: A comparative study," Annals of Surgery 184:594–600.

*Primary Examiner*—Michael G. Wityshyn
*Assistant Examiner*—Jane Williams
*Attorney, Agent, or Firm*—Pennie & Edmonds

[57] ABSTRACT

The present invention relates to a living skin replacement. In particular, it relates to a biosynthetic dressing material composed of a living stromal tissue prepared from stromal cells such as fibroblasts cultured upon a three-dimensional framework and a transitional covering which acts as an epidermal replacement. Such a living skin replacement provides long-term biologic coverage of full-thickness wound defects. Since human fibroblasts are known to be relatively non-antigenic when transferred to allogeneic hosts, a temporary living skin replacement made up of such cells attached to a transitional covering may replace the use of cadaveric skin allografts for achieving temporary wound closure in cases where the patients lack enough healthy skin for autografts.

12 Claims, 11 Drawing Sheets

TEMPORARY LIVING SKIN REPLACEMENT

The present application is a continuation-in-part of U.S. patent application Ser. No. 08/131,361, filed Oct. 4, 1993; which is a division of U.S. patent application Ser. No. 07/575,518, filed Aug. 30, 1990 now U.S. Pat. No. 5,266,480; which is a division of U.S. patent application Ser. No. 07/402,104, filed Sep. 1, 1989 now U.S. Pat. No. 5,032,508; which is a continuation-in-part of U.S. patent application Ser. No. 07/242,096, filed Sep. 8, 1988 now U.S. Pat. No. 4,963,489; which is a continuation-in-part of U.S. patent application Ser. No. 07/038,110, filed Apr. 14, 1987 (abandoned); which is a continuation-in-part of U.S. patent application Ser. No. 07/036,154, filed Apr. 3, 1987 now U.S. Pat. No. 4,721,096; which is a continuation of U.S. patent application Ser. No. 06/853,569, filed Apr. 18, 1986 (abandoned), each of which is incorporated by reference herein in its entirety.

TABLE OF CONTENTS

1. INTRODUCTION
2. BACKGROUND OF THE INVENTION
3. SUMMARY OF THE INVENTION
4. BRIEF DESCRIPTION OF THE DRAWINGS
5. DETAILED DESCRIPTION OF THE INVENTION
    5.1. ESTABLISHMENT OF THREE-DIMENSIONAL STROMAL TISSUE
    5.2. SUITABLE TRANSITIONAL COVERING MATERIALS
    5.3. USES OF STROMAL TISSUE/TRANSITIONAL COVERING
6. EXAMPLE: DEVELOPMENT OF A TEMPORARY LIVING SKIN REPLACEMENT COMPOSED OF HUMAN FIBROBLASTS CULTURED ON "BIOBRANE"
    6.1. MATERIALS AND METHODS
        6.1.1. PREPARATION OF THE LIVING SKIN REPLACEMENT
        6.1.2. APPLICATION OF "BIOBRANE"/HF GRAFTS TO ATHYMIC MICE
        6.1.3. TISSUE PREPARATION AND HISTOLOGIC ANALYSIS
        6.1.4. QUANTIFICATION OF CYTOKINE-SPECIFIC mRNA
    6.2. RESULTS

1. INTRODUCTION

The present invention relates to a living skin replacement. In particular, it relates to a biosynthetic dressing material composed of a living stromal tissue prepared from stromal cells such as fibroblasts cultured upon a three-dimensional framework and a transitional covering which acts as an epidermal replacement. Such a living skin replacement provides long-term biologic coverage of full-thickness wound defects. Since human fibroblasts are known to be relatively non-antigenic when transferred to allogeneic hosts, a temporary living skin replacement made up of such cells attached to a transitional covering may replace the use of cadaveric skin allografts for achieving temporary wound closure in cases where the patients lack enough healthy skin for autografts.

2. BACKGROUND OF THE INVENTION

Approximately 10,000 people in the United States die from severe burns every year. Life-threatening burns occur in significant numbers in every form of military engagement and at every level of service. A critical need exists to improve survival rates and the standard of care for such burned patients and to reduce costs of treatment.

Surgical excision of the burn wound and application of an autograft taken from the patient's unburned skin is the routine method to treat patients with extensive burn injuries in the United States. Alternatively, when only small areas of unburned autograft skin are available for wound coverage, human cadaveric skin allograft, either cryopreserved or fresh, is currently the standard biologic dressing for coverage of extensive excised burn wounds (Atnip and Burke, 1983, Curr Prob. Surg. 20:623–86; Pruitt and Levine, 1984, Arch. Surg. 119:312–22; Hansbrough, 1987, In: Boswick J, ed. *The Art and science of Burn Care*. Rockville, Md.: Aspen Publ. Inc., 57–63). The performance of cryopreserved allograft skin on wounds is inferior to that of fresh skin, probably due to the loss of viability of keratinocytes and fibroblasts following cryopreservation, freezing and subsequent thawing. In addition, disruption of some of the physical composition of skin, such as basement membrane structures, by cryopreservation procedures may also contribute to decreased cell viability.

While fresh cadaveric skin allograft is the superior covering for excised wounds when autograft skin is not available, fresh skin is in limited supply. Another problem with cadaveric allograft skin is that it elicits host immunological rejection within several weeks of placement, although survival may be prolonged in the severely burned patient who become markedly immune suppressed secondary to the injury (Ninnemann et al., 1978, Transplantation 25:69–72). In patients with massive burn injury, this poses a significant problem because several months may be required for limited donor sites to heal in order to permit reharvesting of the patient's own skin for autografts to accomplish complete wound closure. Rapid rejection of allograft skin would necessitate its repeat application; unfortunately, rejection is frequently accompanied by bacterial colonization and infection of the wounds which can limit subsequent engraftment of both allogeneic and autologous skin. Additionally, subsequent allograft applications frequently undergo accelerated rejection, as a result of previous sensitization of the recipient's immune system. Care of patients with extensive burns thus becomes a race against time to achieve adequate graft coverage before life-threatening infections and other complications occur. Consequently, in this haste, the autograft skin is usually meshed and stretched widely so that it can cover large wound areas. Such meshing and stretching always result in extensive and unsightly mesh patterns of the healed skin, with accompanying scarring and contractions that remain permanently. This may even require reconstructive surgery over many years.

Other problems also accompany the use of cadaveric allograft skin. The costs and complexities of managing clinical skin banks are considerable (May and DeClement, 1981, J Burn Care Rehab 2:7–23; May and DeClement, 1981, J. Burn Care Rehab. 2:64–76; May and DeClement, 1981, J Burn Care Rehab 2:128–41), resulting in high costs of allograft skin (usually from $.50 to $1.00 per cm2), a price which frequently does not cover the actual costs of skin procurement, preservation, storage and distribution and quality-control. Allograft skin, particularly fresh, is in short supply due to limited numbers of referred and qualifying donors.

In addition, the potential for infectious disease transmission accompanying the use of cadaveric allograft skin is always present. Infection may be in the form of bacteria (Monafo and Bradley, 1976, J. Am. Med. Assoc. 235:1248–9; Blood et al., 1979, Proc. 11th Am. Burn Assoc.

Mtg. 79–80; White et al., 1991, Am. Surg. 57:402–7; May and DeClement, 1981, J. Burn Care Rehab. 2:64–76), fungi or viruses (Simonds et al., 1992, N. Engl. J. Med. 326:726–32; Clarke, 1987, Lancet 1:983). In particular, human immunodeficiency virus (HIV) transmission is possible even with properly-screened skin, since the donor may have been infected but is tested during a period when the viral infection is not detectable in the blood utilizing current assays (Simonds et al., 1992, N. Engl. J. Med. 326:726–32). In view of the foregoing problems with cadaveric skin, there is a need for a superior alternative temporary skin replacement for the treatment of extensively burned patients. Ideally, such a substitute for cadaveric skin should adhere to the wound rapidly and reproducibly, persist long-term without rejection, and be readily available in large amounts.

3. SUMMARY OF THE INVENTION

The present invention relates to a temporary living skin replacement, methods for preparing it, and methods of using it, particularly in the treatment of extensively burned patients.

The invention is based, in part, on Applicants' discovery that human stromal cells can be grown on a three-dimensional framework which is bonded to a transitional covering, and used for burn coverage in vivo. The temporary living skin replacement of the invention comprises the three-dimensional living stromal tissue bonded to a transitional covering, including but not limited to silicone or polyurethane membrane. The temporary living skin replacement of the present invention is exemplified herein using an ultrathin silicone rubber membrane of "BIOBRANE" as a transitional covering which replaces the epidermal layer of skin. The "BIOBRANE" covering is semipermeable to water vapor and gases, but impermeable to the passage of microorganisms. Additionally, this outer transitional covering is mechanically bonded to an underlying living dermal tissue composed of human neonatal fibroblasts (HF) cultured on a three-dimensional knitted nylon mesh. In the working examples described infra, the "BIOBRANE"/HF living grafts are transferred to full-thickness, excised wounds on athymic mice and demonstrated to function as effective full-thickness skin replacements. Upon placement on a wound site, such "BIOBRANE"/HF grafts secrete collagen, fibronectin and cytokines, and tightly adhere to the wound bed with dense underlying vascular ingrowth for extended periods of time. Therefore, such living stromal tissue/transitional covering may be prepared in advance and stored, ready for immediate clinical use as a temporary living skin replacement. The potential combination of a transitional covering with cultured autologous keratinocytes to provide permanent skin coverage offers a further advantage.

4. BRIEF DESCRIPTION OF THE DRAWINGS

FIG. 1 A schematic outline of the preparatory steps for producing the temporary living skin replacement.

Figure 2A:

FIG. 2A Histologic preparation of "BIOBRANE" cultured with human fibroblasts after 9 days of culture and examined at ×400. The graft has no integral strength, and easily fragments and disrupts during processing and sectioning procedures, partially due to shearing from the brittle nylon fibers. Arrows indicate nylon fibers of the "BIOBRANE" sectioned transversely.

Figure 2B:
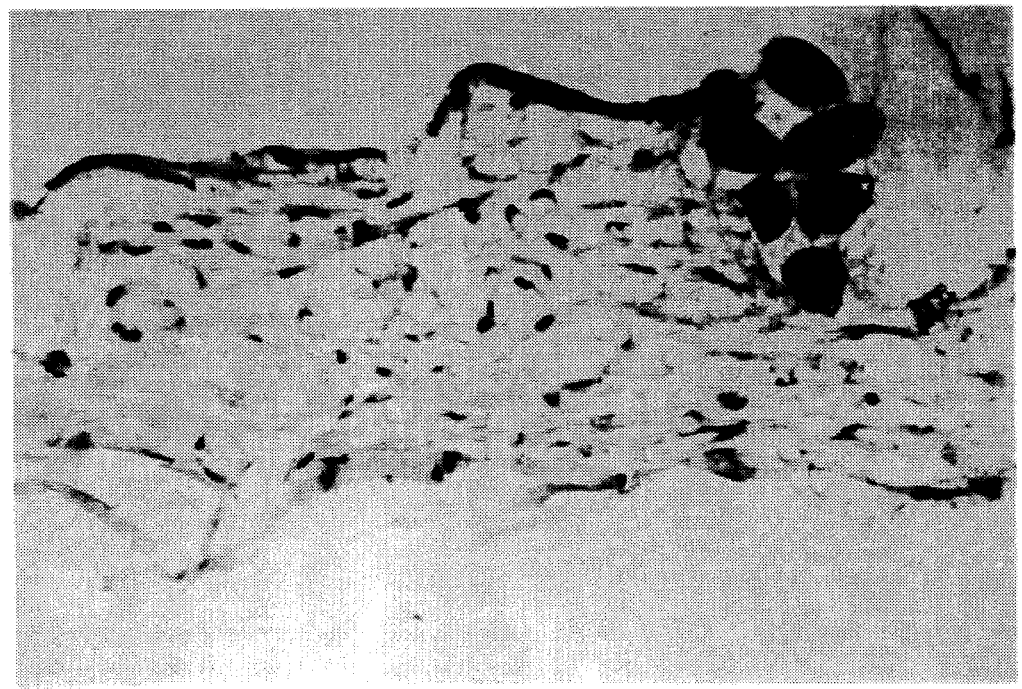

FIG. 2B Histologic preparation of "BIOBRANE" cultured with human fibroblasts after four weeks of culture and examined at ×200. The graft has much greater structural integrity, presumably from secreted matrix proteins, and maintains its integrity during processing and sectioning procedures. Arrows indicate nylon fibers of the "BIOBRANE" sectioned transversely.

Figure 3A:
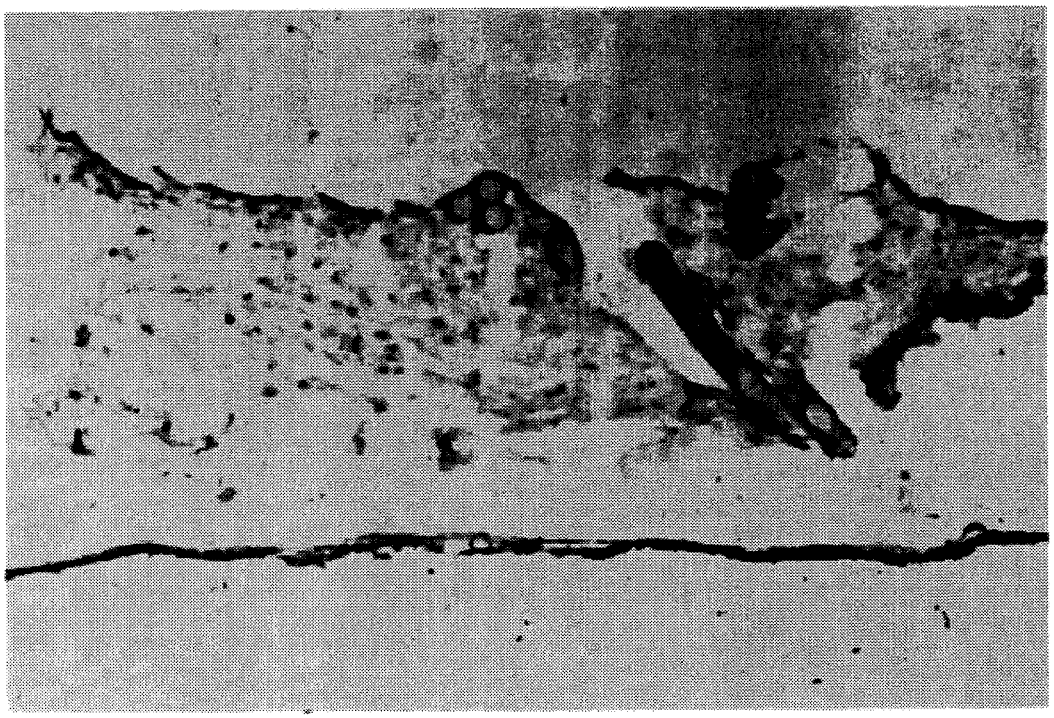

FIG. 3A Immunohistochemical staining for fibronectin in "BIOBRANE"/HF tissue constructs after 4 weeks of culture. This figure shows a negative control stained with the secondary antibody alone.

Figure 3B:
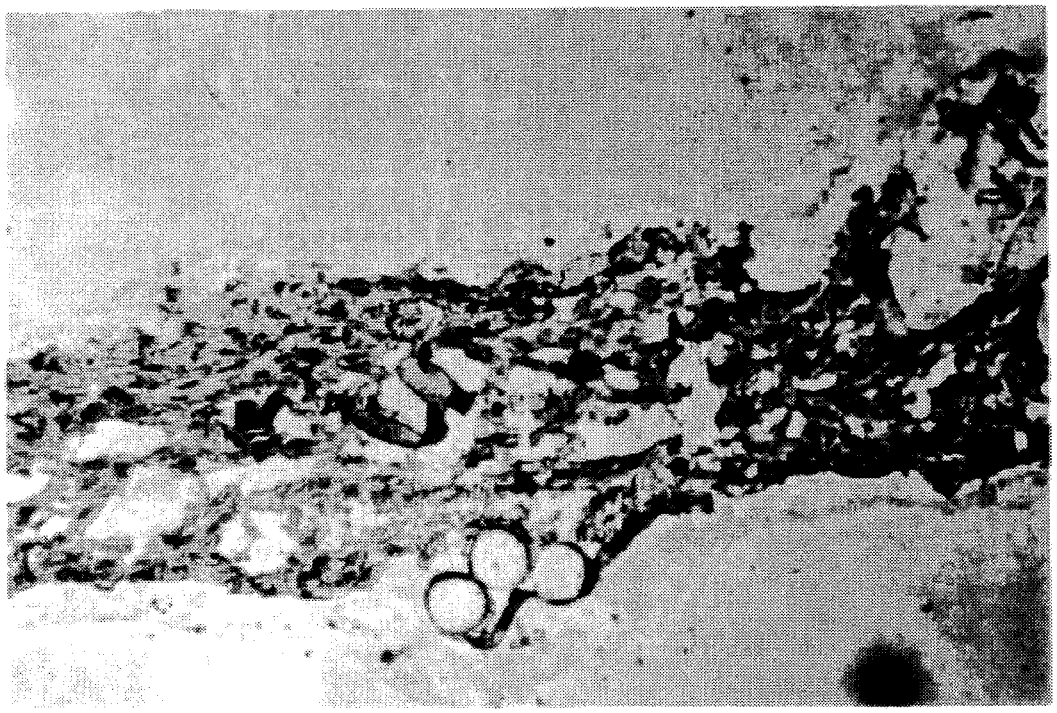

FIG. 3B Immunohistochemical staining for fibronectin in "BIOBRANE"/HF tissue constructs after 4 weeks of culture. A rabbit anti-human fibronectin antibody is used and the tissue examined at ×200.

Figure 4:
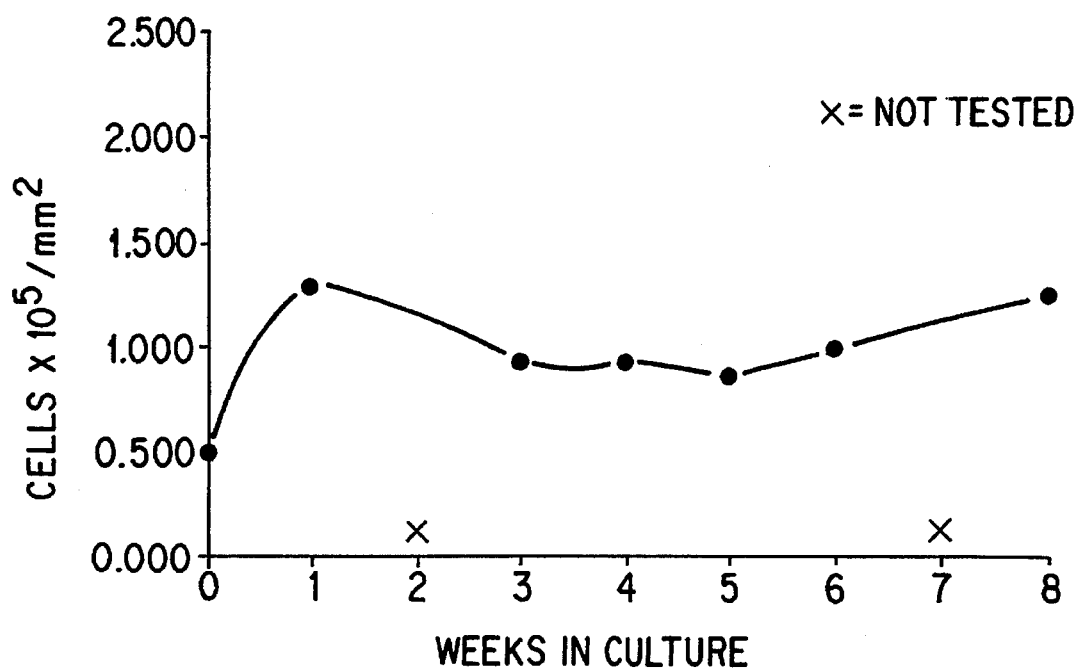

FIG. 4 Fibroblast cell numbers in graft constructs at intervals after inoculation of HF on "BIOBRANE". Each point represents the mean of three separate determinations.

Figure 5:
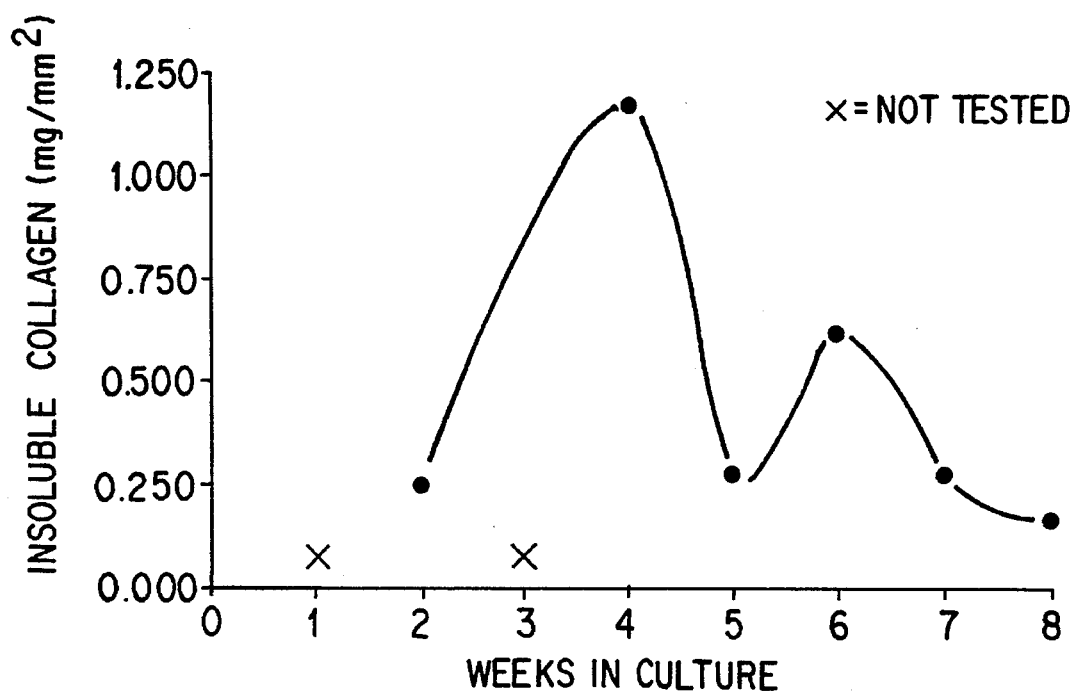

FIG. 5 Quantitation of type I collagen deposition in cultured grafts after inoculation of HF on "BIOBRANE", by using aniline blue assay. Each point represents the mean of three separate determinations.

Figure 6:
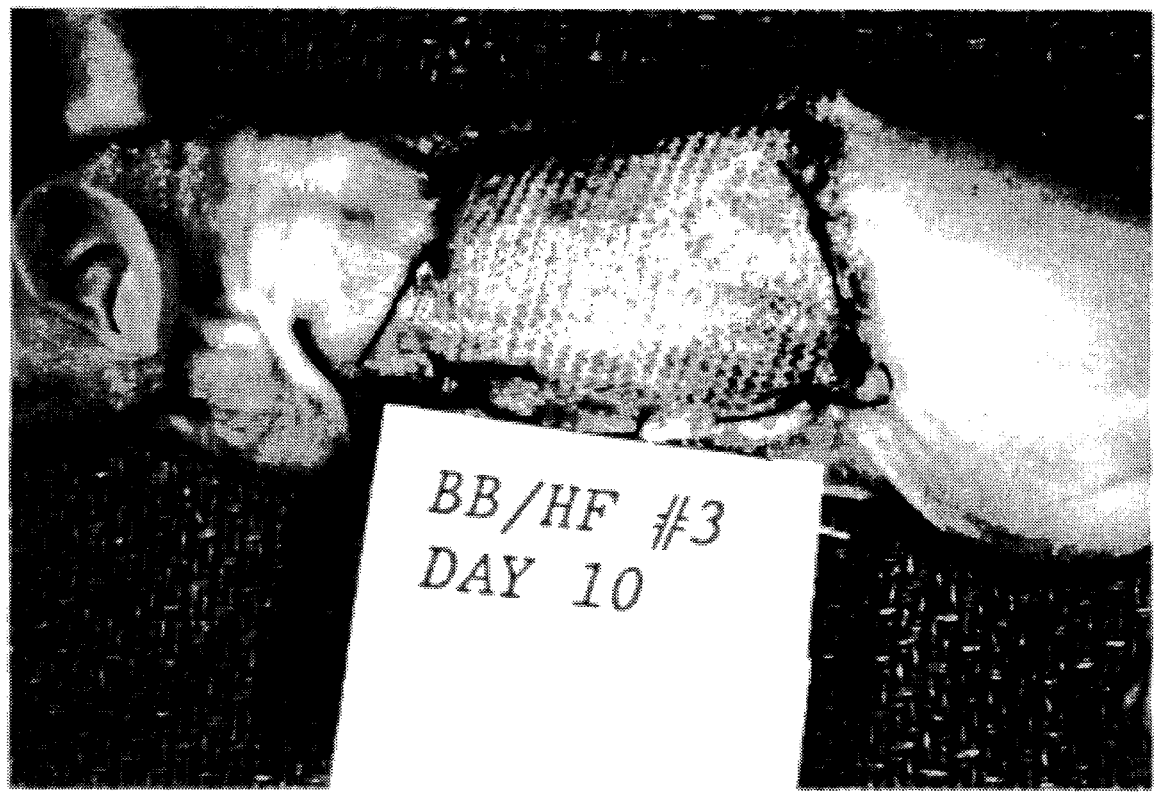

FIG. 6 At day 10 following placement on a full-thickness wound on an athymic mouse, the "BIOBRANE"/HF graft is tightly adherent to the wound bed with no fluid collections, and has developed a pink color which blanches with pressure.

Figure 7:
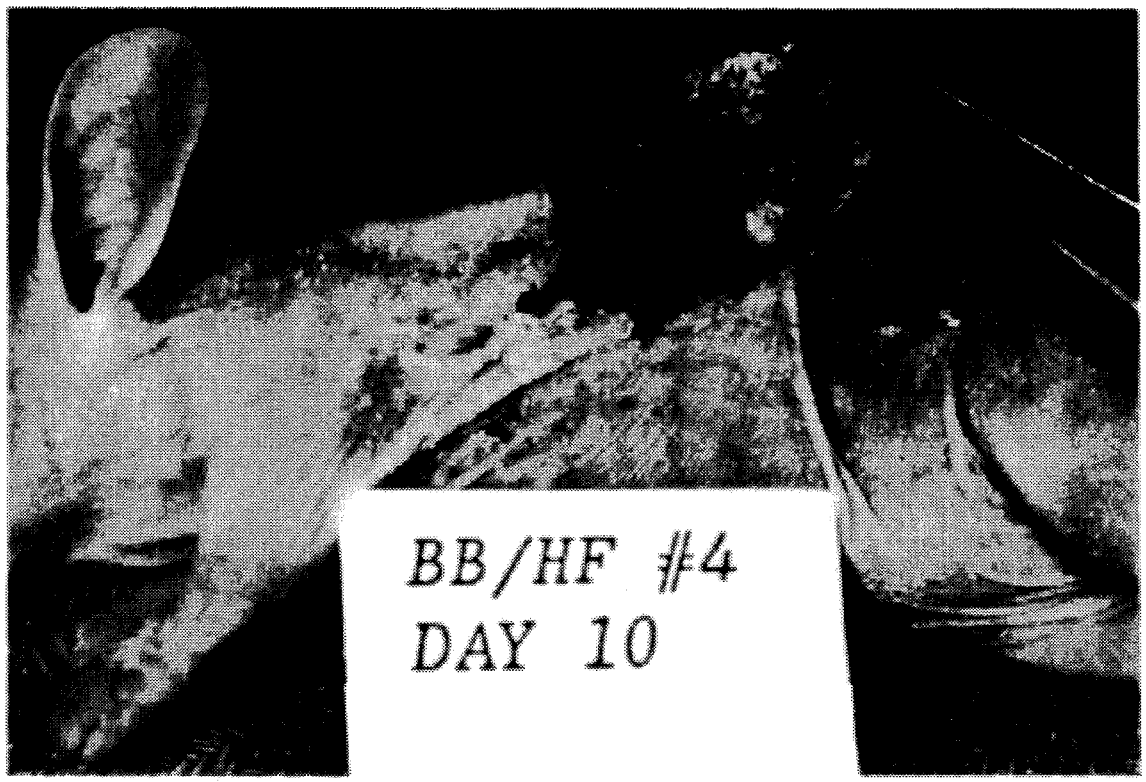

FIG. 7 At day 10 following placement on a full-thickness wounds on an athymic mouse, a "BIOBRANE"/HF graft is shown being pulled away from the wound, resulting in bleeding and tearing of the underlying tissues reflecting dense fibrovascular ingrowth from the wound bed into the graft. Similar ingrowth and attachment are observed at 20, 30 and 40 days post grafting.

Figure 8:
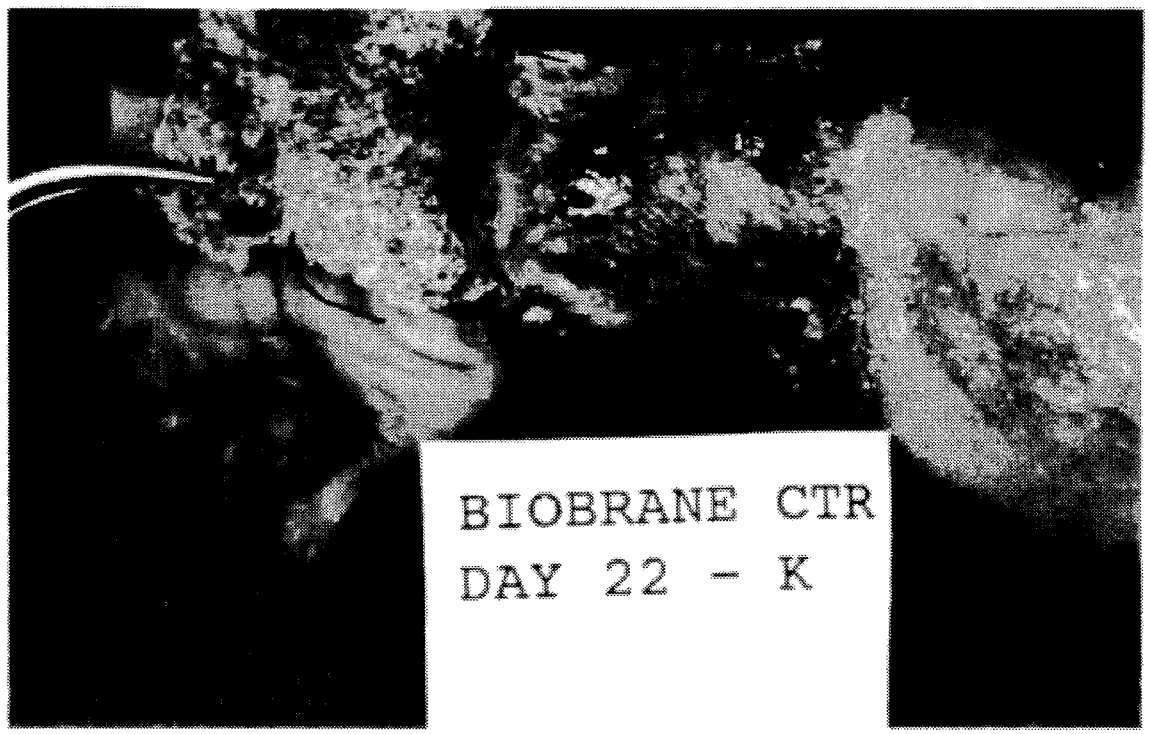

FIG. 8 At day 20 postplacement, a typical "BIOBRANE" control graft is easily separated from the wound; the underlying wound has almost completely closed by contraction and epithelialization.

Figure 9:
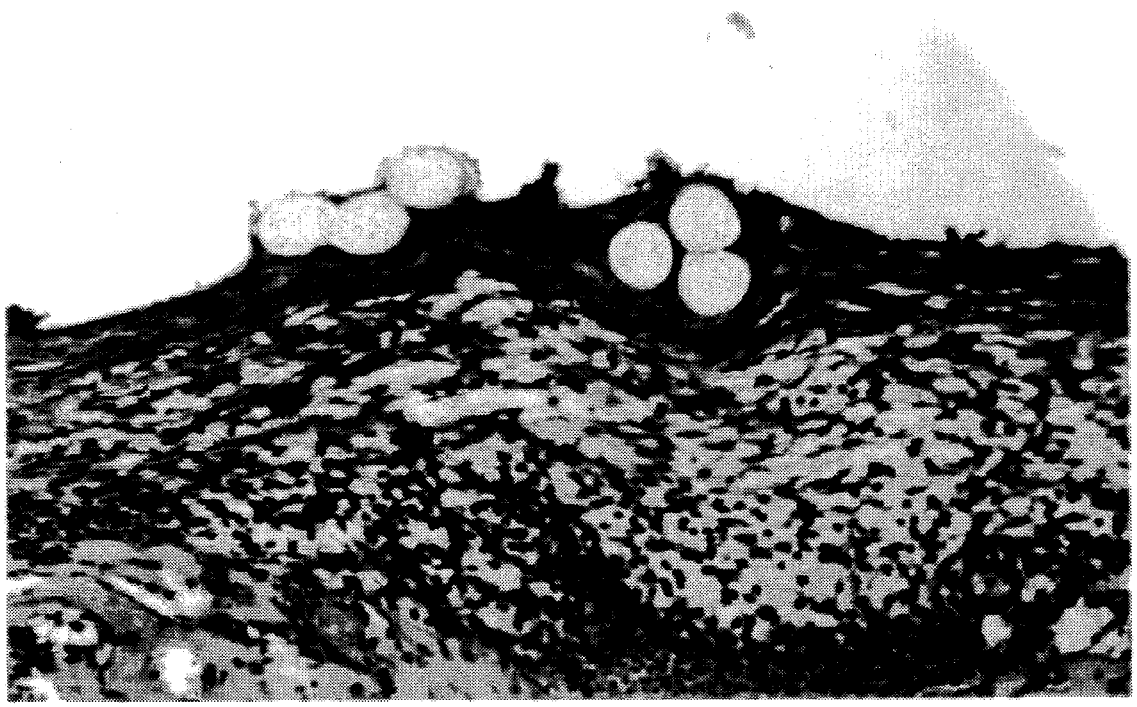

FIG. 9 At day 10 postplacement, histologic examination of a typical "BIOBRANE" control graft reveals a dense collection of inflammatory cells in fluid spaces and host tissue beneath the dressing. There is no evidence of vascular ingrowth.

Figure 10:
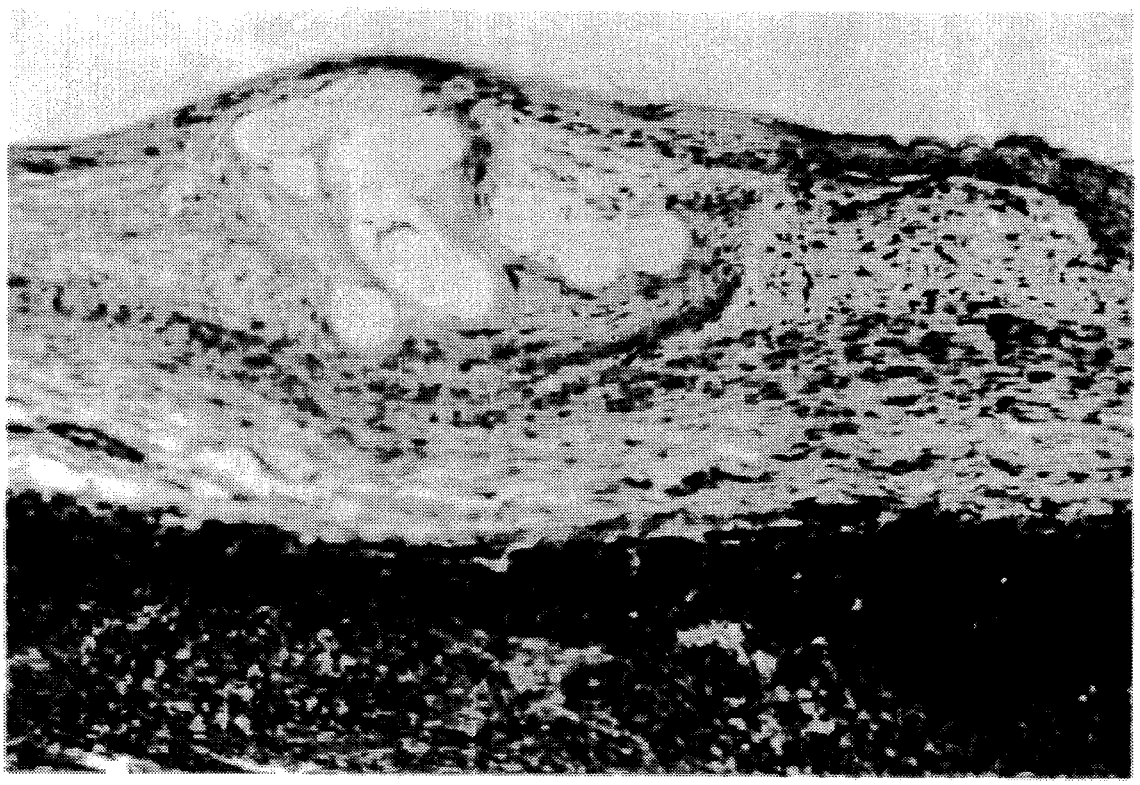

FIG. 10 At day 10 postplacement, histologic examination of a typical "BIOBRANE"/HF graft reveals vascular ingrowth into the fibroblast-matrix with minimal inflammatory cell infiltration. Blood vessels are denoted by the arrows.

Figure 11:

FIG. 11 At day 20 postplacement, histologic examination of a typical "BIOBRANE"/HF graft reveals an increase in vascular ingrowth as denoted by the arrows, with no evidence of inflammatory cells.

Figure 12:
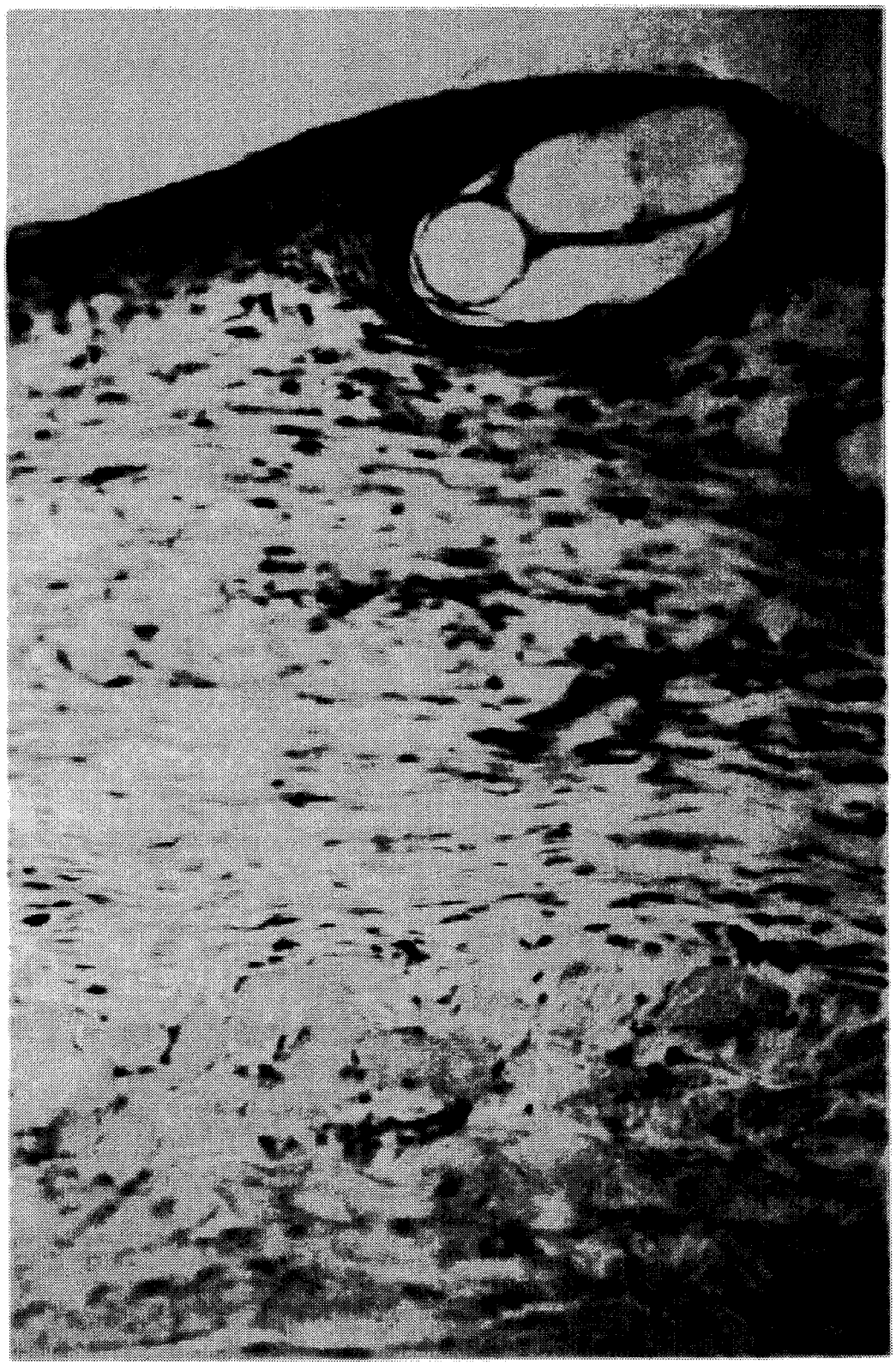

FIG. 12 At day 20 postplacement, a layer of epithelium has formed beneath the silicone membrane. This epidermal ingrowth represents active epithelial ingrowth from the wound edges of the animal, indicating that the tissue environment beneath the synthetic epidermis is highly conducive to epithelial growth.

5. DETAILED DESCRIPTION OF THE INVENTION

The present invention relates to a temporary replacement for human skin using biosynthetic dressing materials which contain a transitional covering as an outer epidermal layer bonded to a framework upon which living human stromal cells are inoculated and allowed to proliferate to form a three-dimensional stromal tissue. In the course of growing and enveloping the framework, the stromal cells secrete large amounts of matrix proteins and cytokines. In a specific embodiment in Example 6, infra, "BIOBRANE" is used as a commercially available synthetic dressing material which consists of a flexible nylon mesh bonded to an ultra-thin silicone rubber layer. Porcine peptides are attached to the nylon mesh because these hydrophilic peptides are apparently critical to successful performance of "BIOBRANE" on wounds (Tavis et al., 1979, Burns 7:123–30). Although "BIOBRANE" has shown a moderate level of efficacy as a temporary wound dressing for coverage of both partial-thickness (Hansbrough et al., 1984, Burns 10:415–9; McHugh et al., 1986, Surgery 100:661–4; Gerding et al., 1988, J. Trauma 8:1265–9) and full-thickness wounds (McHugh et al., 1986, Surgery 100:661–4; Purdue et al., 1987, J. Trauma 27:155–7), its performance for achieving closure of full-thickness wound defects is inferior to that of fresh, highly-viable allograft skin. In fact, in a survey of burn directors in the United States, a majority of them preferred using fresh cadaver skin for wound coverage compared to cryopreserved skin or "BIOBRANE"(Greenleaf and Hansbrough, 1994, Amer. Burn Assoc. 26th meeting).

Example 6, infra, shows that neonatal fibroblasts for the preparation of the skin replacement may be obtained from donors used for preparation of a living dermal replacement ("DERMAGRAFT", Advanced Tissue Sciences, La Jolla, Calif.) (Cooper et al., 1991, Biomaterials 12:243–8; Hansbrough et al., 1992, Surgery 111:438–46; Landeen et al., 1992, Wounds 4:167–75) which is currently in multi-center clinical trials (Hansbrough et al., 1992, J. Burn Care Rehab. 13:519–29). Both the fibroblast infant donor and the mother are screened for infectious agents, including HIV, both prior to tissue acquisition and at intervals thereafter. The cultured cells are also screened at intervals using highly sophisticated viral assays, including the use of molecular probes and the polymerase chain reaction. The isolated fibroblasts are cryopreserved without further in vitro propagation until results of all screens are negative. Thus the potential for infectious disease transmission from the cultured cells is minimized.

Extensive clinical experience suggests that human fibroblasts are relatively non-antigenic and do not readily induce immediate rejection following transfer to allogeneic hosts (Hansbrough et al., 1992, J. Burn Care Rehab. 13:519–29; Cuono et al., 1986, Lancet 1:1123–4; Heck et al., 1985, J. Trauma 25:106–12; Hickerson and Compton, 1991, Proc. 23rd Am. Burn Assoc. Mtg. 7). When the living stromal tissue/transitional covering graft is placed on a wound site of an athymic mouse, no evidence of graft rejection is noted over the 40 day study period. Thus, the living stromal tissue/transitional covering graft may also be non-antigenic when transferred to wounds on allogeneic human hosts, in which case graft persistence may be limited only by durability of the nylon mesh and of the silicone rubber layer, which could last for several months.

The animal studies exemplified in Example 6, infra, indicate that the addition of living fibroblasts to "BIOBRANE" markedly improves the adherence of the dressing to the wound bed and results in long term survival of this biosynthetic living skin replacement. In fact, successful wound adherence occurs in over 97% of the cases and for over 40 days. Studies of human fibroblasts cultured on a "VICRYL" (polyglactic acid) mesh as a dermal support have shown that this material ("DERMAGRAFT") contains matrix proteins and various growth factors such as fibroblast growth factor, platelet-derived growth factor, and insulin-like growth factors (Landsen et al., 1992, Wounds 4:167–75). The living stromal tissue/transitional covering of the present invention is also shown to contain normal constituents of human skin, including type I collagen and fibronectin. Cytokines and growth factors are also present since the "BIOBRANE"/HF grafts exemplified herein are prepared under similar culture conditions as "DERMAGRAFT". Thus, the living stromal tissue/transitional covering may bear remarkable structural and functional similarity to living skin grafts, with the exception that the keratinocyte layer is replaced by a layer of synthetic epidermis. Furthermore, the cryopreserved grafts are as effective as the fresh cadaveric grafts in achieving wound closure.

When the temporary living skin replacement of the present invention persists clinically following placement on excised wounds, the burn patient could undergo early excision followed by immediate coverage with this long-term cultured skin replacement. At intervals thereafter, the patient could be returned to surgery where areas of the wounds could undergo excision of the living stromal tissue/transitional covering graft followed by coverage with autograft skin as donor sites heal and become available. Alternatively, successful temporary wound coverage with living stromal tissue/transitional covering could permit the three to four week (or longer) time interval required for laboratory preparation of large areas of cultured skin substitutes of various types (Hansbrough, 1992, Wound Coverage with Biologic Dressings and Cultured Skin Substitutes. RG Landes Co., Austin, Tex.), including cultured autologous epithelial sheets (Odessey, 1992, J. Burn Care Rehab. 13:174–80) or composite cultured autologous grafts which contain both epidermal and dermal elements (Hansbrough et al., 1989, J. Am. Med. Assoc. 262:2125–30; Cooper and Hansbrough, 1991, Surgery 109:198–207; Cooper et al., 1993, J. Invest. Dermatology 101:811–819).

The invention is discussed in more detail in the subsections below, solely for purposes of description and not by way of limitation. For clarity of discussion, the specific procedures and methods described herein are exemplified using neonatal foreskin fibroblasts and "BIOBRANE", but they are merely illustrative for the practice of the invention. Analogous procedures and techniques are equally applicable, and stromal cells from any tissue sources may be cultured on any suitable dressing material to form a living stromal tissue/transitional covering for the practice of the invention.

5.1. ESTABLISHMENT OF THREE-DIMENSIONAL STROMAL TISSUE

The temporary living skin replacement of the present invention is composed of stromal cells such as fibroblasts cultured upon a three-dimensional framework bonded to a transitional covering as a synthetic epidermis to form a living stromal tissue/transitional covering. In general, the transitional covering is made up of a semipermeable membrane bonded to a three-dimensional support framework upon which the cells are incubated and grown. The three-dimensional support framework may be of any material and/or shape that: (a) allows cells to attach to it (or can be modified to allow cells to attach to it); and (b) allows cells to grow in more than one layer. A number of different materials may be used to form the framework, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE; TEFLON), thermanox (TPX), nitrocellulose, cotton, polyglycolic acid (PGA), cat gut sutures, cellulose, gelatin, dextran, etc. A convenient nylon mesh which could be used in accordance with the invention is Nitex, a nylon filtration mesh having an average pore size of 210 μm and an average nylon fiber diameter of 90 μm (#3-210/36, Tetko, Inc., N.Y.). Any of these materials may be woven into a mesh, to form the three-dimensional framework. These non-degradable materials are suited for cultures that are to be maintained for long periods of time or cryopreserved.

Certain materials, such as nylon, polystyrene, etc., are poor substrates for cellular attachment. When these materials are used as the three-dimensional support matrix, it is advisable to pre-treat the framework prior to inoculation of stromal cells in order to enhance the attachment of stromal cells to the framework. For example, prior to inoculation with stromal cells, nylon matrices could be treated with 0.1M acetic acid, and incubated in polylysine, FBS, elastic fibers, reticular fibers, collagen, glycosaminoglycans (e.g., heparan sulfate, chondroitin sulfate, dermatan sulfate, keratan sulfate, etc.), a cellular matrix, and/or other materials. Polystyrene could be similarly treated using sulfuric acid. In the case of "BIOBRANE" the nylon mesh is coated with porcine peptides.

For in vivo use, it is preferable to use biodegradable frameworks such as polyglactic acid, polyglycolic acid, catgut suture material, or gelatin, for example. In particular, chitin and chitosan may be the preferred materials for constructing a biodegradable framework for in vivo use. Chitin (polyacetyl glucosamine) is the second most widely occurring polysaccharide, being the structural polymer of most crustaceans and fungi. Chitosan (polyglucosamine) is produced by the controlled deacetylation of chitin. Chitin/chitosan are currently used in wound dressings (Bis-chitin, Roussel-Unitika and Tegasorb; 3M Inc, Minneapolis Minn.)) and as a component of hospital bed sheets. Chitin/chitosan have the following biological properties:

a. Hemostasis, causing the agglutination of red cells while not activating either platelets or the intrinsic coagulation system;

b. Cell growth substrate including keratinocytes and fibroblasts;

c. Anti-microbial activity; and d. Wound healing and anti-scarring by delaying collagen formation.

Glucosamine and acetyl glucosamine monomers are known cell nutrients, hence the ultimate breakdown products of both chitin and chitosan make a positive contribution to cell growth and would healing. Hyaluronic acid, a key component in extracellular matrix development, particularly in the embryo but also in early stages of healing, is an alternating copolymer of glucosamine with a low incidence of the acetyl derivative, and glucuronic acid; thus there are compelling reasons to focus on glucosamine and its acetyl derivative as cell growth substrates.

Chitosan can be produced in a wide range of molecular weights by alkali treatment. Although chitosan is insoluble at pH 7 above 20,000 Daltons, the polymer dissolves in dilute acetic or lactic acid and fibers can be spun into weak baths containing bicarbonate (East et al., 1988, 4 Int. Conf. Chitin/Chitosan, Trondheim). Resulting fibers are subject to degradation by enzymes capable of breaking the β-gycosidic bond; lysozyme is particularly effective. Simple hydrolysis also becomes an important degradation mechanism as the chain length decreases.

Additionally, N.O. carboxymethyl chitosan (NOCC), formed by treating chitosan under alkaline conditions with mono-chloracetic acid, has similar structure to hyaluronic acid and is soluble in water. NOCC forms strong films when cast from water and can be spun into fibers using coagulation baths containing $Ca^{+2}$, $Zn^{+2}$ or other similar di- or trivalent cations. Fibers formed have similar but greater water absorbency characteristics to alginate fibers. NOCC is highly biocompatible and biodegradable. A variable matrix of fibers for cell growth substrate can be assembled by knitting a mixture of chitosan and NOCC fibers together. These technologies are available at Innovative Technologies Inc., Cheshire, United Kingdom.

Stromal cells comprising fibroblasts, with or without other cells and elements are inoculated onto the three-dimensional framework bonded to a transitional covering. These fibroblasts may be derived from any organs but preferably skin which can be obtained by biopsy (where appropriate) or upon autopsy. In fact, fibroblasts can be obtained in quantity rather conveniently from many organs. In particular, neonatal or fetal fibroblasts can be used to form a "generic" three-dimensional stromal tissue that will support the growth of a variety of different cells and/or tissues. However, a "specific" stromal tissue may be prepared by inoculating the three-dimensional framework with fibroblasts derived from the same type of tissue to be cultured and/or from a particular individual who is later to receive the cells and/or tissues grown in culture.

Fibroblasts may be readily isolated by disaggregating an appropriate organ or tissue which is to serve as the source of the fibroblasts. This may be readily accomplished using techniques known to those skilled in the art. For example, human neonatal foreskin samples can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, dispase etc. Mechanical disruption can also be accomplished by a number of methods including, but not limited to the use of grinders, blenders, sieves, homogenizers, pressure cells, or insonators to name but a few. For a review of tissue disaggregation techniques, see Freshney, Culture of Animal Cells. A Manual of Basic Technique, 2d Ed., A.R. Liss, Inc., New York, 1987, Ch. 9, pp. 107–126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. For a review of clonal selection and cell separation techniques, see Freshney, Culture of Animal Cells. A Manual of Basic Techniques, 2d Ed., A.R. Liss, Inc., New York, 1987, Ch. 11 and 12, pp. 137–168.

The isolation of fibroblasts may, for example, be carried out as follows: fresh tissue samples are thoroughly washed and minced in Hanks balanced salt solution (HBSS) in order to remove serum. The minced tissue is incubated from 1–12 hours in a freshly prepared solution of a dissociating enzyme such as trypsin. After such incubation, the dissociated cells are suspended, pelleted by centrifugation and plated onto culture dishes. All fibroblasts will attach before other cells, therefore, appropriate stromal cells can be selectively isolated and grown. The isolated fibroblasts can then be grown to confluency, lifted from the confluent culture and inoculated onto the three-dimensional framework bonded to a transitional covering (see, Naughton et al., 1987, J. Med. 18(3&4):219–250). Inoculation of the three-dimensional framework with a high concentration of stromal cells, e.g., approximately $10^6$ to $5 \times 10^7$ cells/ml, may result in the establishment of the three-dimensional stromal tissue in shorter periods of time.

In addition to fibroblasts, other stromal cells may be added to form the three-dimensional stromal tissue required to support long term growth in culture. For example, other cells found in loose connective tissue may be inoculated onto the three-dimensional support along with fibroblasts. Such cells include but are not limited to endothelial cells, pericytes, macrophages, monocytes, plasma cells, mast cells, adipocytes, etc. Although these stromal cells may readily be derived from appropriate organs such as skin, liver, etc., using methods known in the art such as those discussed above, stromal cells which are specialized for the particular tissue to be cultured, i.e., skin in the instant case, may be added to the fibroblast stroma.

After inoculation of the stromal cells, the three-dimensional framework should be incubated in an appropriate nutrient medium. Many commercially available media such as DMEM, RPMI 1640, Fisher's, Iscove's, McCoy's, and the like may be suitable for use. It is important that the three-dimensional stromal tissue be suspended in the medium during the incubation period in order to maximize proliferative activity. In addition, the culture spent media should be replaced periodically by fresh media. In an effort to avoid the presence of foreign proteins, serum-free media may also be used.

During the incubation period, the stromal cells will grow linearly along and envelop the three-dimensional framework before beginning to grow into the openings of the framework. The openings of the framework should be of an appropriate size to allow the stromal cells to stretch across the openings. Maintaining actively growing stromal cells which stretch across the framework enhances the production of growth factors and extracellular matrix proteins by the stromal cells. For example, if the openings are too small, the stromal cells may rapidly achieve confluence but be unable to easily exit from the mesh; trapped cells may exhibit contact inhibition and cease production of the appropriate factors necessary to support vascular ingrowth in vivo. If the openings are too large, the stromal cells may be unable to stretch across the opening; this will also decrease stromal cell production of the appropriate factors. When using a mesh type of matrix, as exemplified herein, openings ranging from about 150 μm to about 220 μm work satisfactorily. However, depending upon the three-dimensional structure and intricacy of the framework, other sizes may work equally well. In fact, any shape or structure that allows the stromal cells to stretch and continue to replicate and grow for lengthy time periods will work in accordance with the invention.

Different proportions of the various types of collagen deposited on the framework may affect the growth of the later infiltrating tissue-specific cells in vivo. For three-dimensional dermal culture systems, collagen types I and III are preferably deposited in the initial framework. Type I collagen is produced by fibroblasts, reticular cells, smooth muscle and connective tissue. Type III collagen is produced by fibroblasts and reticular cells. The proportions of collagen types deposited can be manipulated or enhanced by selecting fibroblasts which elaborate the appropriate collagen type. This can be accomplished using monoclonal antibodies of an appropriate isotype or subclass that is capable of activating complement, and which define particular collagen types. These antibodies and complement can be used to negatively select the fibroblasts which express the desired collagen type. Alternatively, the stroma used to inoculate the support can be a mixture of cells which synthesize the appropriate collagen types desired.

During incubation of the three-dimensional stromal support, proliferating cells may be released from the framework. These released cells may stick to the walls of the culture vessel where they may continue to proliferate and form a confluent monolayer. This should be prevented or minimized, for example, by removal of the released cells during feeding, or by transferring the dressing material with the attached three-dimensional stromal tissue to a new culture vessel. The presence of a confluent monolayer in the vessel may "shut down" the growth of cells in the three-dimensional framework and/or culture. Removal of the confluent monolayer or transfer of the framework to fresh media in a new vessel will restore proliferative activity of the three-dimensional culture system. Such removal or transfers should be done in any culture vessel which has a stromal monolayer exceeding 25% confluency. Alternatively, the culture system could be agitated to prevent the released cells from sticking, or instead of periodically feeding the cultures, the culture system could be set up so that fresh media continuously flows through the system. The flow rate could be adjusted to both maximize proliferation within the three-dimensional culture, and to wash out and remove cells released from the framework, so that they will not stick to the walls of the vessel and grow to confluence. In any case, the released stromal cells can be collected and cryopreserved for future use.

5.2. SUITABLE TRANSITIONAL COVERING MATERIALS

The present invention is directed to a living stromal tissue/transitional covering as a temporary living skin replacement. This replacement mimics the natural skin by having two basic components: a living underlying dermal tissue covered by an artificial epithelium consisting of a semipermeable membrane. The invention is exemplified using "BIOBRANE". However, the invention is not limited to the use of this dressing material. For example, one disadvantage in the use of "BIOBRANE" for this purpose is that its outer silicone membrane is perforated. Therefore, another type of nonperforated ultrathin layer such as polyurethane may be used to furnish a better barrier to microorganisms and to have a higher moisture vapor transmissions (MVTRs). The materials suitable for use as a transitional covering include any semi-permeable membrane that has a high MVTR characteristics.

Normal skin has a range of moisture vapor transport rates of 200–2000 $g.m.^{-2}.d^{-1}$ (Lamke et al., 1977, Scand. J. Clin. Lab. Invest. 37:325). Damaged skin, as in burns, may result in elevated water loss as high as 3000–5000 $g.m.^{-2}.d^{-1}$ (Lamke et al., 1971, Scand. J. Plast. Surg. 5:17; Lamke et al., 1977, Burns 3:159; Cohen, 1966, Plast. Recon. Surg. 37:475; Barr et al., 1969, Scand. J. Plast. Recon. Surg. 3:30). Conventional hydrophobic polyether urethane films with equilibrium water contents of <1% have MVTRs of 1500–2000 $g.m.^{-2}.d^{-1}$. However, when coated with a conventional medical adhesive, the MVTR falls to 500–1000 g.m.$^{-2}$.d$^{-1}$ because the adhesive blocks the transmission of water vapor. Conventional films with working MVTRs of <1000 g.m.$^{-2}$.d$^{-1}$ are unsatisfactory for use on medium or high exuding wounds since accumulation of exudates occurs. This leads to maceration of tissues, channeling and leakage, and potentiates infections.

Hydrophilic films potentially solve the pooling problem. Any hydrophilic polymer film will hydrate in the presence of water (exudate). The degree of hydration depends on the amount of water (exudate) available; the hydration is almost 100% reversible. The MVTR of the hydrophilic polymer film is dependent upon the degree of hydration; i.e., the MVTR increases as the film hydrates and decreases as the degree of hydration falls. This variability can therefore be used to maintain an optimum healing environment since a dressing produced from a hydrophilic film can respond to changing conditions of exudate.

A typical member of this family of films, Polyurethane 425, is produced by Innovative Technologies Inc. The polyurethane membrane supports the attachment and growth of a variety of cells types including fibroblasts. Neonatal human fibroblasts and keratinocytes have been seeded onto the surface of these polyurethane membranes, both cell types attach and proliferate on the membranes, similar to their behavior on plastic tissue culture flask surfaces. Polyurethane membranes can be bonded to knitted meshes made of various materials including chitosan, for use in the present invention.

5.3. USES OF STROMAL TISSUE/TRANSITIONAL COVERING

The present invention also encompasses a temporary living skin replacement composed of a non-perforated outer layer such as polyurethane as transitional covering with a living dermis cultured upon a biodegradable polysaccharide mesh. This particular composition has several advantages in its use. The polyurethane membrane has a very high MVTR similar to normal epidermis, and thus limits fluid accumulation. As the polysaccharide fibers degrade by hydrolysis over several weeks after placement on a wound bed, the outer layer can be simply peeled away to expose the neodermis, because polyurethane itself has a low adherence to the wound. The "neodermis" may remain in the wound to improve subsequent engraftment. This approach would alleviate the need for surgical excision to remove a temporary skin replacement, which should greatly simplify the clinical procedure.

Another advantage of the present invention is the potential utility for combining with cultured keratinocytes (cultured epithelial autografts, or CEA) to achieve permanent wound closure. Since CEA grafting to burn patients was first reported (Gallico et al., 1984, N. Engl. J. Med. 311:448), many clinical reports have described CEA for covering burn wounds (Hansbrough, 1992, Wound Coverage With Biologic Dressing and Cultured Skin Substitutes RG Landers Co. Austin, Tex.). Unfortunately, "take" of CEA is as low as 13%, and durability of healed skin has been problematic probably because of slow development of important attachment structures at the dermal-epidermal junction (DEJ).

In another embodiment of the present invention, cultured keratinocytes may be injected beneath the transitional covering 1-2 wks after the grafts are placed on a wound. Results with the Biobrane/HF grafts indicate that the interface between the synthetic "epidermis" and the underlying "neodermis") promote epithelial ingrowth from the wound margins; this phenomenon is probably accelerated by growth factors in the tissue. Utilization of this technique should permit application of autologous keratinocytes to a sterile, hospitable wound environment which will support further epithelial growth in vivo. As the keratinocytes proliferate and become confluent beneath the polyurethane membrane, the membrane should lift away as a chitosan fibers degrade, leaving a permanantly resurfaced wound with a rich neodermis.

Alternatively, human keratinocytes may be cultured on biocompatible transitional covering. The covering carrying attached keratinocytes may then be placed on "neodermis" resulting from removal of the first covering following placement of grafts on excised wounds.

The technique of injecting cells beneath the transitional covering has a high potential utility compared to the transfer of cells on membranes. In clinical use on burn patients, autologous keratinocytes could be injected following their establishment in culture to select high percentages of proliferating cells (as low as 1% of keratinocytes may form colonies when plated on plastic). Thus the wound bed could be "seeded" in situ with highly proliferating epidermal cells. Further propagation of the cells would then occur in vivo in a protected environment beneath the semi-permeable membrane which appears to be highly conducive to epidermal growth.

6. EXAMPLE: DEVELOPMENT OF A TEMPORARY LIVING SKIN REPLACEMENT COMPOSED OF HUMAN FIBROBLASTS CULTURED ON "BIOBRANE"

6.1. MATERIALS AND METHODS
6.1.1. PREPARATION OF THE LIVING SKIN REPLACEMENT

Human dermal fibroblasts were isolated from human neonatal foreskin samples. The epidermis and dermis were separated by incubation in 0.25% trypsin/0.2% EDTA for 1 to 2 hours at 37° C. Dermis was minced and digested with collagenase B, and the tissue digest was filtered through sterile gauze to remove debris. Fibroblasts were maintained in plastic tissue culture dishes in Dulbecco's Modified Eagle's Medium (DMEM) containing 10% fetal bovine serum, and were passaged when the cells reached 80% to 90% confluence on the plastic. Fibroblasts were removed from flasks and resuspended for seeding at a concentration of $4 \times 10^6$ cells/ml. Living grafts were prepared by seeding $5 \times 10^5$ viable fibroblasts, with viability determined by trypan blue exclusion, in a minimum volume of DMEM onto each 10×10 cm section of "BIOBRANE" II Green Label (Dow Hickam Inc., Sugar Land, Tex.). The "BIOBRANE" was maintained with the silicone-bonded surface down in culture medium and with the nylon mesh side on top. The fibroblasts attached in vitro to the mesh fibers and became confluent in 4 to 5 weeks, i.e., all nylon mesh openings were covered by cells and tissue matrix as observed by inverted phase microscopy. Representative samples of the "BIOBRANE"/ human fibroblast grafts ("BIOBRANE"/HF) were taken at intervals from the culture medium and prepared for histologic analysis. FIG. 1 outlines the preparatory steps for the temporary living skin replacement.

6.1.2. APPLICATION OF "BIOBRANE"/HF GRAFTS TO ATHYMIC MICE

Animal experiments were performed with approval of the University of California, San Diego, Animal Research Committee and in accordance with guidelines prepared by the Committee on Care and Use of Laboratory Animals of the Institute of Laboratory Animal Resources, National Research Council. Athymic mice, BALB/c nu/nu (Simonsen Laboratories, Gilroy, Calif.) were kept in isolation rooms.

Surgery and dressing changes were performed in laminar-flow hoods under anesthesia with 10 mg intraperitoneal (i.p.) Avertin (Aldrich Chemical Company, Milwaukee, Wis.) in 0.4 ml of normal saline. The dorsolateral surface of the mouse was washed with povidone-iodine and 70% isopropanol. A 2 by 2 cm full-thickness skin section was excised, sparing the panniculus carnosus, and wound margins were tattooed with india ink. The excision resulted in a 15% to 20% body surface area skin defect.

2 by 2 cm sections of "BIOBRANE" or "BIOBRANE"/HF were placed on the wound and sutured to the wound edges with 6-0 silk. Generally, the grafts were transferred to wounds after 4 to 5 weeks of fibroblast growth in vitro. A tie-over dressing was created with the silk sutures, which anchored the graft to the wound. Animals were given daily injections of 3 mg ceftazidime (Eli Lilly Inc., Indianapolis, Ind.) i.p. for 7 days after surgery. Sulfamethoxazole and trimethoprim (Biocraft Laboratories, Elmwood Park, N.J.) were added to autoclaved drinking water. Mortality rates of grafting procedures was approximately 5%. There were 5 to 6 animals in each experimental group for analysis on each of days 5, 10 and 20 postgrafting; 2–3 animals were utilized for observations at days 30 and 40 postgrafting. 35 mice received "BIOBRANE" control dressings. Animals were examined for integrity of dressings each day and were killed on postsurgical days 5, 10 and 20, 30 and 40, at which time the animals were photographed and tissue was obtained for histologic analysis.

6.1.3. TISSUE PREPARATION AND HISTOLOGIC ANALYSIS

Sections of the in vitro "BIOBRANE"/HF grafts were fixed in phosphate-buffered 10% formalin, dehydrated in ethanol, cleared in xylene, and embedded in paraffin overnight. Embedded tissues were sectioned on a rotary microtome at 3 µm thickness and stained with hematoxylin and eosin. The nylon fibers made histologic sectioning of the in vitro cultured grafts difficult and the specimens tore easily during cutting, particularly during the first few weeks of fibroblast growth on the "BIOBRANE" fabric. After several weeks, the in vitro "BIOBRANE"/HF grafts had much greater structural integrity, and they sectioned more easily with less disruption.

Tissue samples from the animal wounds were obtained by excising the entire graft with a surrounding rim of normal mouse skin and underlying panniculus carnosus, fascia and muscle. Samples were fixed, sectioned and stained with hematoxylin and eosin as described above.

Type I collagen in the in vitro "BIOBRANE"/HF grafts was identified by staining with a rabbit anti-human type I collagen antibody (Chemicon Inc., Temecula, Calif.), followed by a secondary antibody goat anti-rabbit IgG coupled to streptavidin-peroxidase (Zymed, S. San Francisco, Calif.). The slides were then developed with hydrogen peroxide and the chromogen, aminoethyl carbazole (Zymed). Fibronectin in the in vitro grafts was identified with a rabbit anti-human fibronectin antibody, and the slides were developed similarly with the secondary reagents.

Collagen matrix deposition was quantitated in cultured grafts by using the aniline blue dye of the Masson trichrome stain. Type I collagen (Sigma Chemical Company) was used for constructing the standard curve. Small squares of cultured grafts were lysed in Triton X-100 (1% in phosphate buffered saline solution, 1 hour). The lysate was removed, and the squares with remaining extracellular matrix were fixed in 10% formalin-phosphate-buffered saline solution. The squares were washed with alcohol and water, then phosphomolybdic acid:phosphotungatic acid:dH$_2$O (1:1:2) mordant (Sigma Chemical Company) (0.5 ml, 15 minutes) was added. This solution was aspirated, and aniline blue dye (aniline blue:H$_2$O 1:2) (Sigma Chemical Company) was added (0.5 ml, 15 minutes). The graft squares were washed with dH$_2$O until the water was clear (three to five times) followed by acetic acid wash (2 ml, 5 minutes). The dye was extracted with 95% ethanol (1 ml, 1 hour). Two hundred µl extracts were placed in wells of a 96-well mictotiter plate, and the absorbance of 590 nm was determined with an enzyme-linked immunosorbent assay plate reader. Collagen type I (Sigma Chemical Company) was used to construct a standard curve.

6.1.4. QUANTIFICATION OF CYTOKINE-SPECIFIC mRNA

Total RNA was extracted from pieces of "BIOBRANE"/HF approximately 2×4 cm in size according to the method of Chomoczynski and Sacci (1987, Anal. Biochem. 162:156). The "BIOBRANE"/HF was rinsed in phosphate buffered saline and cut into pieces approximately ¼ inch square prior to processing. One ml guanidinium thiocyanate solution was added to the samples and they were vortexed and sonicated in a sonicating water bath for 10 min. The samples were centrifuged at 14,000 g for 10 min to remove the support structure and the supernatant was collected in a 1 cc syringe with a 25 gauge needle. The guanidinium thiocyanate solution containing cells and cell debris was then forced through the needle to break up the chromosomal DNA. 100 µl of 3M ammonium acetate was added along with 0.5 ml of phenol and 0.5 ml of chloroform. One µg of total RNA in 5.0 µl of water was heated to 65° C. for 5 min, placed on ice and combined with 5.0 µl of reverse transcriptass (RT) mix containing 0.02 mg/ml oligo-DT, 1 µg acetylated bovine serum albumen, 0.8 µl Moloney murine leukemia virus reverse transcriptase, 2.0 µl First Strand Buffer (Gibco Inc., Grand Island N.Y.), 1.0 mM deoxyribonucleoside triphosphate, 0.1 mM dichlorodiphenyl trichloroethane, and 8,000 U RNasin (Promega, Madison, Wis.). The reaction mixture was then incubated at 37° C. for 1 hr to allow cDNA synthesis. Polymerase chain reaction (PCR) for mRNA encoding acidic and basic fibroblast growth factors (a/bFGFs), transforming growth factor (TGF), keratinocyte growth factor (KGF), platelet-derived growth factor (PDGF) and GAPDH which is an intracellular "housekeeping" enzyme, were performed using 2.5 µl of the cDNA generated by RT is described above. The PCR reaction mixture contained 0.2 mM dNTP, 10 pM primers, 2.5 mM magnesium and 0.025 U taq polymerase in PCR buffer (Perkin Elmer Cetus, Norwalk, Conn.). mRNA for these growth factors was amplified on a Perkin Elmer Cetus 9600 in a total volume of 25 ml over 35 cycles which included heating to 94° C. for denaturation, cooling to 67° C. for annealing, and 75° C. for extension. Upon completion of amplification, the PCR products were stained with ethidium bromide and then electrophoresed in agarose gels and analyzed by scanning densitometry using the LKB Bromma Densitometer (Pharmacia, Uppsala Sweden). Comparisons between samples were based on total amount of RNA added to each reverse transcription reaction and relative amount of GADPH message.

6.2. RESULTS

Sequential phase microscopic examination of grafts in culture and histologic preparations of the in vitro grafts showed that following seeding of the "BIOBRANE", the human fibroblasts slowly attached to the nylon mesh over a period of several days, and proliferated during the first one to three weeks. During the initial three weeks, the "BIOBRANE"/HF grafts had little structural integrity, and when embedded and sectioned it tore and fragmented easily, apparently due to the hard and brittle nature of the nylon fibers (FIG. 2A). However, between three and five weeks of culture the number of fibroblasts and the degree of protein deposition in the nylon fabric appeared to have substantially increased, as evidenced by microscopic evaluation of cell numbers under phase contrast illumination and the degree of eosinophilic staining of the intercellular spaces of living tissue construct (FIG. 2B). In addition, after sequential weeks of culture the living grafts were more easily sectioned with less disruption of the nylon fabric and the cultured tissue construct became more opague. By five weeks following inoculation of fibroblasts, examination of "BIOBRANE"/HF grafts by immunohistochemical staining revealed heavy deposition of fibronectin in the spaces between the nylon fibers (FIG. 3A and 3B). Staining for type I collagen and decorin showed similar results.

Fibroblast cell numbers in the living grafts and quantitation of the deposition of type I collagen are depicted in FIGS. 4 and 5. Cell numbers remained relatively stable after the first week of culture, whereas collagen deposition markedly increased from the second week to the fourth week and then declined, perhaps reflecting remodeling of the tissue construct.

Following placement of grafts onto the animal wounds, both the "BIOBRANE" and "BIOBRANE"/HF grafts appeared to adhere initially to the wound beds when grafts were first examined on day 5 postplacement. However, by day 10 many of the "BIOBRANE" grafts developed subgraft fluid collections. "BIOBRANE"/HF grafts remained tightly adherent to the wounds on day 10 (FIG. 6), and forceful peeling of the grafts from the wound resulted in tearing and active bleeding of the wound bed tissue due to apparent tissue ingrowth into the grafts (FIG. 7). Peeling of the "BIOBRANE" grafts on day 10 resulted in much easier separation from the wound bed with minimal bleeding.

By day 20 many of the "BIOBRANE" grafts were separating from the wound surface, the underlying wounds were approximately 50% reduced in area at this time, due to apparently both contraction and epithelialization processes (FIG. 8). In contrast, "BIOBRANE"/HF grafts remained tightly adherent to the wounds on days 20, 30 and 40 postgrafting, and significant forces were required to separate the dressings from the wound at these time points, again resulting in extensive tissue disruption and bleeding from the underlying wound.

Histologic examination of "BIOBRANE"-covered wounds at all time points revealed marked inflammatory collections, which appeared to consist of both neutrophils and mononuclear cells (FIG. 9). Little evidence of vascular ingrowth into the "BIOBRANE" dressing was noted. In contrast, histologic examination of "BIOBRANE"/HF-covered wounds revealed minimal or no inflammatory reactions at any of the time points and evidence of progressive incorporation of the living graft into the wound bed tissue (FIG. 10). At 20 and 40 days postgrafting, the wound bed and the "BIOBRANE"/HF graft formed essentially a tissue continuum with many fibroblasts, evidence of ground substance deposition which stained with eosin, and a rich vascular network with minimal or no inflammatory cell responses (FIG. 11).

Of particular interest, a confluent layer of keratinocytes became evident in most animals, immediately beneath the silicone membrane, by the third week postgrafting (FIG. 12). It was thought that this layer represented fibroblasts and was perhaps reflecting the formation of a fibroblast "capsule" beneath the silicone layer; however, stains for keratin indicated that this layer was composed of keratinocytes. No human keratinocytes were presumably transferred with the grafts, since the culture conditions for creation of the grafts were extremely hostile to keratinocytes. Therefore this layer of epithelium must have originated from the murine epidermis at the wound margins, indicating that the wound environment beneath the silicone membrane was extremely conducive to the growth of keratinocytes. This may be due to the high levels of growth factors including keratinocyte growth factor in the microenvironment.

Using reverse transcriptase, polymerase chain reaction technology, various growth factor mRNA levels in the "BIOBRANE"/HF were quantified from band densities on gel scans; each (+) indicates 10-fold increase in mRNA level. Levels of GAPDH (an intracellular "housekeeping" enzyme) mRNA were used to normalize amounts of the various tissue samples. The amounts of cytokine mRNAs in the tissue constructs were compared to levels in adult and neonatal skin; the mRNA profile paralleled neonatal skin samples, while adult skin specimens demonstrated remarkably low levels of cytokine-specific mRNA (Table 1).

TABLE 1

QUANTIFICATION OF CYTOKINE-SPECIFIC MESSENGER RNA IN "BIOBRANE"/HF GRAFTS

|  | aFGF | bFGF | $TGF_{alpha}$ | $TGF_{beta}$ | KGF | PDGF | GAPDH |
| --- | --- | --- | --- | --- | --- | --- | --- |
| 1) Neonatal skin | 0 | +++ | +++ | +++ | ++ | ++ | +++++ |
| 2) "BIOBRANE"/HF | ++++ | ++ | ++ | ++++ | +++ | 0 | +++++ |
| 3) Adult Skin | ++ | 0 | +++ | 0 | 0 | ++ | +++++ |

The "BIOBRANE"/HF living grafts showed structural and functional similarity to living neonatal split-thickness skin, with metabolically active fibroblasts in a living dermal tissue containing secreted and deposited matrix proteins, and high levels of mRNA for multiple trophic cytokines; while the "epithelium" was composed of a low-permeability silicone membrane.

"BIOBRANE"/HF grafts were cryopreserved in 10% DMSO using computer-run controlled-rate freezing equipment, and stored for several days to several weeks in liquid nitrogen. Mitochondrial activity assessed by the MTT assay (Triglia et al., 1991, In Goldberg (ed) Alternative Methods in Toxicology Vol. 8 Mary Ann Liebert Inc., New York, pp 351–362; Triglia et al., 1991, Toxic in Vitro 5:573–578) was found to have decreased approximately 40% which is routine for cryopreservation of human skin. Cryopreserved and thawed grafts were then placed on excised wounds on 80 athymic mice. The grafts adhered and provided wound coverage for as long as 40 days in over 90 of animals. No difference between their performance as compared with fresh grafts, could be seen.

The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A temporary living skin replacement comprising a living stormal tissue substantially enveloping a framework which is prepared in vitro and a transitional covering bonded to the living stromal tissue, which stromal tissue comprises stromal cells and connective tissue proteins naturally secreted by the stromal cells and which framework is composed of a biocompatible, non-living material formed into a three dimensional structure having interstitial spaces bridged by said stromal cells.

2. The temporary living skin replacement of claim 1 in which the stromal cells are fibroblasts.

3. The temporary living skin replacement of claim 1 in which the stromal cells are a combination of fibroblasts, endothelial cells, pericytes, macrophages, monocytes, leukocytes, plasma cells, mast cells and adipocytes.

4. The temporary living skin replacement of claim 1 in which the framework is composed of a biodegradable material.

5. The temporary living skin replacement of claim 4 in which the biodegradable material is polyglactic acid, chitin, chitosan, cotton, polyglycolic acid, cat gut structures, cellulose, gelatin or dextran.

6. The temporary living skin replacement of claim 1 in which the framework is composed of a non-biodegradable material.

7. The temporary living skin replacement of claim 6 in which the non-biodegradable material is a polyamide, a polyester, a polystyrene, a polypropylene, a polyacrylate, a polyvinyl, a polycarbonate, a polytetrafluorethylene or nitrocellulose compound.

8. The temporary living skin replacement of claim 4, 5, 6 or 7 in which the framework is pre-coated with collagen.

9. The temporary living skin replacement of claim 8 in which the framework is a mesh.

10. The temporary living skin replacement of claims 1, 2, 3, 4, 5, 6 or 7 in which the framework is a mesh.

11. The temporary living skin replacement of claim 1 in which the transitional covering is made of silicone.

12. The temporary living skin replacement of claim 1 in which the transitional covering is made of polyurethane.

* * * * *